US011892290B2

(12) United States Patent
Nakamura

(10) Patent No.: US 11,892,290 B2
(45) Date of Patent: Feb. 6, 2024

(54) OPTICAL COHERENCE TOMOGRAPHY APPARATUS, IMAGING METHOD, AND NON-TRANSITORY COMPUTER READABLE MEDIUM STORING IMAGING PROGRAM

(71) Applicant: NEC Corporation, Tokyo (JP)

(72) Inventor: Shigeru Nakamura, Tokyo (JP)

(73) Assignee: NEC CORPORATION, Tokyo (JP)

(*) Notice: Subject to any disclaimer, the term of this patent is extended or adjusted under 35 U.S.C. 154(b) by 247 days.

(21) Appl. No.: 17/291,071

(22) PCT Filed: Oct. 31, 2019

(86) PCT No.: PCT/JP2019/042930
§ 371 (c)(1),
(2) Date: May 4, 2021

(87) PCT Pub. No.: WO2020/100626
PCT Pub. Date: May 22, 2020

(65) Prior Publication Data
US 2021/0389116 A1 Dec. 16, 2021

(30) Foreign Application Priority Data
Nov. 12, 2018 (JP) ................ 2018-212046

(51) Int. Cl.
*G01B 9/02* (2022.01)
*G01B 9/02091* (2022.01)
(Continued)

(52) U.S. Cl.
CPC ..... *G01B 9/02091* (2013.01); *G01B 9/02043* (2013.01); *G01B 9/02044* (2013.01);
(Continued)

(58) Field of Classification Search
CPC ............ G01B 9/02091; G01B 9/02043; G01B 9/02044; G01B 9/02085; G01B 9/02087;
(Continued)

(56) References Cited

U.S. PATENT DOCUMENTS

2012/0133950 A1* 5/2012 Suehira ............. G01B 9/02019
356/479
2012/0294500 A1 11/2012 Utsunomiya et al.
(Continued)

FOREIGN PATENT DOCUMENTS

JP 2010-250466 A 11/2010
JP 2011156035 A 8/2011
(Continued)

OTHER PUBLICATIONS

Machine translation of JP 2011-158309 (Year: 2011).*
(Continued)

*Primary Examiner* — Uzma Alam
*Assistant Examiner* — Jonathon Cook
(74) *Attorney, Agent, or Firm* — Sughrue Mion, PLLC

(57) ABSTRACT

An optical coherence tomography apparatus includes a branching and merging device that branches a light beam emitted from a wavelength sweeping laser light source into an object light beam and a reference light beam, a balanced photodetector that generates information about a change in an intensity ratio of interference light beams, which are generated by the interference between the object light beam and the reference light beam, wherein the object light beam is scattered from the measurement object after being transmitted through the transparent substrate including a structure that changes a thickness, and a control unit that acquires structural data of the measurement object in a depth direction based on the information about the change in the intensity ratio of the interference light beams and connects
(Continued)

the structural data while moving an irradiation position of the object light beam with a position of the above structure as a reference.

12 Claims, 8 Drawing Sheets

(51) Int. Cl.
    *G01N 21/47*     (2006.01)
    *A61B 3/10*     (2006.01)
    *A61B 3/12*     (2006.01)
    *A61B 5/00*     (2006.01)
    *A61B 5/1172*     (2016.01)
    *G01N 21/17*     (2006.01)

(52) U.S. Cl.
    CPC .............. *G01N 21/47* (2013.01); *A61B 3/102* (2013.01); *A61B 3/12* (2013.01); *A61B 5/0066* (2013.01); *A61B 5/1172* (2013.01); *G01N 2021/1787* (2013.01)

(58) Field of Classification Search
    CPC ............ G01B 9/02056; G01B 9/02058; G01N 21/47; G01N 2021/1787; A61B 3/102; A61B 3/12; A61B 5/0066; A61B 5/1172
    See application file for complete search history.

(56) References Cited

U.S. PATENT DOCUMENTS

2015/0363630 A1    12/2015  Hogan
2017/0083742 A1    3/2017  Lamare et al.

FOREIGN PATENT DOCUMENTS

| JP | 2011158309 A | 8/2011 |
| JP | 2012110575 A | 6/2012 |
| JP | 2013-022338 A | 2/2013 |
| JP | 2018173301 A | 11/2018 |
| WO | 2012017231 A1 | 2/2012 |
| WO | 2017125570 A1 | 7/2017 |

OTHER PUBLICATIONS

International Search Report of PCT Application No. PCT/JP2019/042930 dated Jan. 21, 2020.

JP Office Action for JP Application No. 2022-171289, dated Jul. 4, 2023 with English Translation.

* cited by examiner

--Related Art--

OPTICAL COHERENCE TOMOGRAPHY APPARATUS, IMAGING METHOD, AND NON-TRANSITORY COMPUTER READABLE MEDIUM STORING IMAGING PROGRAM

This application is a National Stage Entry of PCT/JP2019/042930 filed on Oct. 31, 2019, which claims priority from Japanese Patent Application 2018-212046 filed on Nov. 12, 2018, the contents of all of which are incorporated herein by reference, in their entirety.

TECHNICAL FIELD

The present disclosure relates to an optical coherence tomography apparatus, an imaging method, and a non-transitory computer readable medium for storing an imaging program.

BACKGROUND ART

As a technique for performing tomographic imaging in the vicinity of a surface of a measurement object, there is an Optical Coherence Tomography (OCT) technology. In the OCT technology, tomographic imaging of the vicinity of the surface of a measurement object is performed by utilizing interference between a scattered light beam (hereinafter also referred to as a "backscattered light beam") from the inside of the measurement object and a reference light beam when the measurement object is irradiated with a light beam. Recently, applications of the OCT technology to medical diagnosis and industrial product inspection have expanded.

In the OCT technology, a position of a part of the measurement object in an optical axis direction, which is a depth direction, where the object light beam is scattered in the measurement object, i.e., a light scattered point, is identified using interference between the object light beam applied and scattered from the measurement object and the reference light beam. By doing so, structural data spatially decomposed in the depth direction of the measurement object is obtained. In many cases, the object light beam is not reflected by 100% at the surface of the measurement object, and instead propagates to some extent to the inside of the measurement object and then is scattered backward. Therefore, the structural data spatially decomposed in the depth direction inside the measurement object part can be obtained. There are Time Domain (TD-OCT) and Fourier Domain (FD-OCT) methods in the OCT technology. The FD-OCT is more promising in terms of its high speed and high sensitivity. In the FD-OCT method, an interference light spectrum of a wide wavelength band is measured when the object light beam and the reference light beam interfere with each other, and the interference light spectrum is subjected to Fourier transformation to obtain the structural data in the depth direction. As a method for obtaining the interference light spectrum, there are the Spectral Domain (SD-OCT) method using a spectroscope and the Swept Source (SS-OCT) method using a light source for sweeping a wavelength.

Further, by scanning the object light beam in an in-plane direction perpendicular to the depth direction of the measurement object, tomographic structural data spatially decomposed in the in-plane direction and spatially decomposed in the depth direction can be obtained. In this manner, three-dimensional tomographic structural data of the measurement object can be obtained. Usually, the object light beam is scanned by a galvanomirror or the like, and the irradiation position of one object light beam is moved.

The OCT technology has been put into practical use as a tomography apparatus of the fundus oculi in an ophthalmic diagnosis, and its application as a non-invasive tomography apparatus to various parts of a living body is being studied. For example, Patent Literature 1 and 2 disclose a technique of dermal fingerprint reading utilizing OCT.

FIG. 6 shows a typical configuration of an optical coherence tomography apparatus of the SS-OCT method. A wavelength-swept optical pulse is generated from a wavelength sweeping laser light source 501. A light beam emitted from the laser light source 501 passes through a circulator 502 and branched into an object light beam R1 and a reference light beam R2 in a branching and merging device 503. The object light beam R1 passes through a fiber collimator 504 and an irradiation optical system 505 composed of a scan mirror and a lens, and then is applied to a measurement object 200. Next, an object light beam R3 scattered in the measurement object 200 returns to the branching and merging device 503. On the other hand, the reference light beam R2 passes through a reference light mirror 507 and then returns to the branching and merging device 503. Thus, in the branching and merging device 503, the object light beam R3 scattered from the measurement object 200 and the reference light beam R4 reflected from the reference light mirror 507 interfere with each other to obtain interference light beams R5 and R6. Therefore, a ratio of intensity of the interference light beam R5 to that of the interference light beam R6 is determined by a phase difference between the object light beam R3 and the reference light beam R4. The interference light beam R5 passes through the circulator 502 and then input to a two-input balanced photodetector 508, whereas the interference light beam R6 is directly input to the two-input balanced photodetector 508.

The ratio of the intensity of the interference light beam R5 to that of the interference light beam R6 changes according to a wavelength change of the light beam emitted from the wavelength sweeping laser light source 501. Thus, the photoelectric conversion output of the balanced photodetector 508 can be measured as an interference light spectrum. By measuring the interference light spectrum and performing the Fourier transformation on the interference light spectrum, data indicating intensity of the backscattered light (the object light beam) at different positions in the depth direction (a Z direction) can be obtained (hereinafter, an operation of obtaining the data indicating the intensity of the backscattered light beams (the object light beams) in the depth direction (the Z direction) at a certain position of the measurement object 200 will be referred to as a "A-scan").

An irradiation position of an object light beam R1 is moved by the irradiation optical system 505, and the measurement object 200 is scanned. The irradiation optical system 505 repeatedly performs the A-scan operation while moving the irradiation position of the object light beam R1 in a scanning line direction (an X direction) and connecting the measurement results, thereby obtaining a map of the intensity of two-dimensional backscattered light beams (the object light beams) in the scanning line direction and the depth direction as the tomographic structural data (hereinafter, an operation of repeatedly performing the A-scan operation in the scanning line direction (the X direction) and connecting the measurement results is referred to as a "B Scan").

Further, the irradiation optical system 505 repeatedly performs the B-scan operation while moving the irradiation position of the object light beam R1 not only in the scanning line direction but also in a direction (a Y direction) perpendicular to the scanning line, and connects the measurement results, thereby obtaining the three-dimensional tomographic structural data (hereinafter, the operation of repeatedly performing the B-scan operation in the direction (the Y direction) perpendicular to the scanning line and connecting the measurement results is referred to as a "C Scan").

The interference light spectrum of N samples having a center wavelength $\lambda_0$ and a wavelength range $\Delta\lambda$ is acquired in the A-scan, and the interference light spectrum is subject to discrete Fourier transformation, thereby obtaining the structural data in the depth direction using $\lambda_0^2/\Delta\lambda$ as a unit of length. When a period of the A-scan is $\Delta T$ and a speed of the object light beam R1 in the B-scan in the scanning line direction is V, the structural data (the tomographic structural data) in the scanning line direction having $V/\Delta T$ as a unit of length is obtained. That is, the positional accuracy of the three-dimensional tomographic structural data obtained by measurement by OCT is determined by operating conditions such as a wavelength sweeping laser light source and a galvanoscanner.

CITATION LIST

Patent Literature

Patent Literature 1: U.S. Patent Application Publication No. 2015/0363630
Patent Literature 2: U.S. Patent Application Publication No. 2017/0083742

SUMMARY OF INVENTION

Technical Problem

In the tomographic apparatus of the fundus oculi, measurement is performed in a range of about 5 mm square. However, a relatively wide range of measurement is often required in other parts of the living body. For example, in fingerprint reading, measurement of a range of at least about 1.5 cm square is often required. As described above, the positional accuracy of the three-dimensional tomographic structural data obtained by the measurement by OCT is determined by operating conditions such as a wavelength sweeping laser light source and a galvanoscanner. Therefore, variations in the operating conditions affect the positional accuracy. For example, if an initial position of the irradiation position when the irradiation position of the object light beam is moved in the X direction is shifted in each B-scan, the three-dimensional tomographic structural data formed by connecting a plurality of the B-scan data pieces becomes inaccurate. There is also a method of performing a comparison process between B-scan images and connecting them, but this method results in an increase in the amount of processing operation.

An object of the present disclosure is to provide an optical coherence tomography apparatus, an imaging method, and a non-transitory computer readable medium for storing an imaging program, which have positional accuracy which is less susceptible to operating conditions such as a light source.

Solution to Problem

A first example aspect of the present disclosure is an optical coherence tomography apparatus including: a wavelength sweeping laser light source; a first branching unit configured to branch a light beam emitted from the wavelength sweeping laser light source into an object light beam and a reference light beam; an irradiation unit configured to apply the object light beam to a predetermined scanning range of a measurement object; a transparent substrate disposed between the measurement object and the irradiation unit and is configured to be capable of transmitting the object light beam; a measurement unit configured to generate information about a change in an intensity ratio of interference light beams, the interference light beams being generated by the interference between the object light beam and the reference light beam, wherein the object light beam is scattered from the measurement object after being transmitted through the transparent substrate and then being applied to the measurement object; and a control unit configured to acquire structural data of the measurement object in a depth direction based on the information about the change in the intensity ratio of the interference light beams generated by the measurement unit. A structure configured to change a thickness of the transparent substrate is formed on a surface of the transparent substrate, the control unit is configured to control the irradiation unit to acquire a plurality of pieces of the structural data in the depth direction while moving an irradiation position of the object light beam along a direction orthogonal to the depth direction of the measurement object, and the control unit is configured to connect the acquired plurality of pieces of the structural data in the depth direction with a position of the structure formed on the surface of the transparent substrate as a reference.

A second example aspect of the present disclosure is an imaging method including: branching a light beam emitted from a wavelength sweeping laser light source into an object light beam and a reference light beam; applying the object light beam to a predetermined scanning range of a measurement object through a transparent substrate including a structure configured to change a thickness of the transparent substrate formed on a surface of the transparent substrate; generating information about a change in an intensity ratio of interference light beams, the interference light beams being generated by the interference between the object light beam scattered from the measurement object and the reference light beam; acquiring, by a control unit, structural data of the measurement object in a depth direction based on the information about the change in the intensity ratio of the interference light beams; acquiring, by the control unit, a plurality of pieces of the structural data in the depth direction while moving an irradiation position of the object light beam along a direction orthogonal to the depth direction of the measurement object; and connecting, by the control unit, the acquired plurality of pieces of the structural data in the depth direction with a position of the structure formed on the surface of the transparent substrate as a reference.

A third example aspect of the present disclosure is a non-transitory computer readable medium storing an imaging program causing a control unit to execute: a process of acquiring structural data of a measurement object in a depth direction based on information about a change in an intensity ratio of interference light beams, the interference light beams being generated by the interference between an object light beam and the reference light beam, wherein the object light beam is scattered from the measurement object, after the object light beam branched from a light beam emitted from a wavelength sweeping laser light source and then passes through a transparent substrate including a structure configured to change a thickness of the transparent substrate formed on a surface of the transparent substrate and then is applied to a predetermined scanning range of the measurement object, and wherein the reference light beam branched from the light beam emitted from the wavelength sweeping laser light source; a process of acquiring a plurality of pieces of the structural data in the depth direction while moving an irradiation position of the object light beam along a direction orthogonal to the depth direction of the measurement object; and a process of connecting the acquired plurality of pieces of the structural data in the depth direction with a position of the structure formed on the surface of the transparent substrate as a reference.

Advantageous Effects of Invention

It is possible to provide an optical coherence tomography apparatus, an imaging method, and a non-transitory computer readable medium for storing an imaging program, which have positional accuracy which is less susceptible to operating conditions such as a light source.

DESCRIPTION OF EMBODIMENTS

Example embodiments of the present disclosure will be described below with reference to the drawings.

Figure 1:
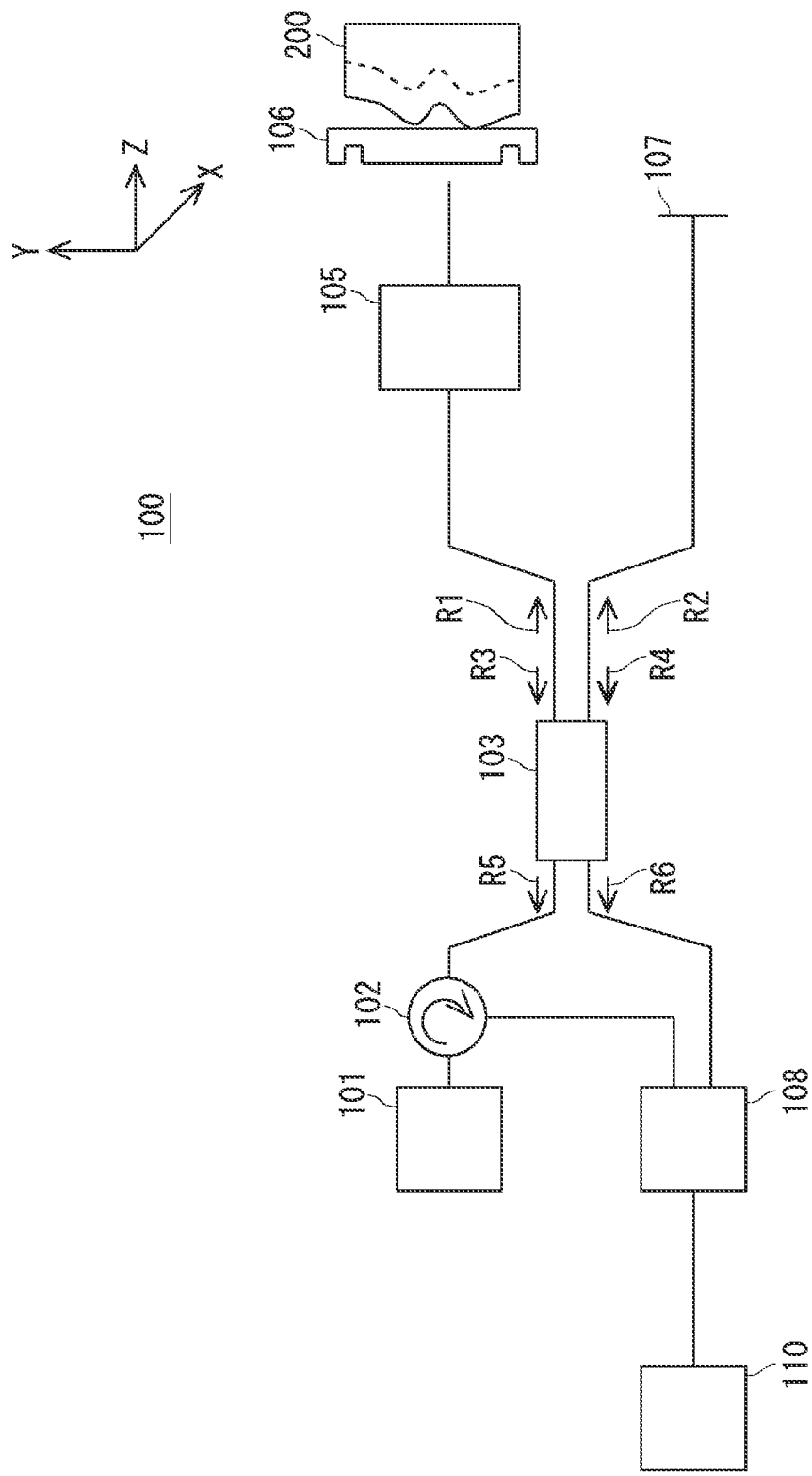
FIG. 1 is a block diagram showing an example of an optical coherence tomography apparatus according to the present disclosure.

FIG. 1 is a block diagram showing an example of an optical coherence tomography apparatus 100 according to the present disclosure. As shown in FIG. 1, the optical coherence tomography apparatus 100 includes a wavelength sweeping laser light source 101, a circulator 102, a branching and merging device 103 serving as a first branching unit, an irradiation optical system 105 serving as an irradiation unit, a transparent substrate with a structure 106, a reference light mirror 107, a balanced photodetector 108 serving as a measurement unit, and a control unit 110, and so on.

A light beam emitted from the wavelength sweeping laser light source 101 is branched into an object light beam R1 and a reference light beam R2 by the branching and merging device 103. The object light beam R1 output from the branching and merging device 103 passes through the irradiation optical system 105 and then enters the transparent substrate with a structure 106.

A structure in which a thickness of the transparent substrate 106 changes (e.g., structures of grooves 106A and 106B and a step 106C, which will be described later) is formed on a surface of the transparent substrate with a structure 106.

The object light beam R1 incident on the transparent substrate with a structure 106 passes through the transparent substrate with a structure 106 and then is applied to a measurement object 200. Then, the object light beam R1 is scattered by the measurement object 200 and scattered backward (in a direction opposite to an irradiation direction of the object light beam R1) from the measurement object 200. Then, an object light beam (a backscattered light beam) R3 scattered from the measurement object 200 passes through the transparent substrate with a structure 106 and the irradiation optical system 105, and then returns to the branching and merging device 503.

The reference light beam R2 output from the branching and merging device 103 is reflected by the reference light mirror 107 and then returns to the branching and merging device 103.

Thus, in the branching and merging device 103, the object light beam R3 scattered from the measurement object 200 and the reference light beam R4 reflected from the reference light mirror 107 interfere with each other to obtain the interference light beams R5 and R6. Therefore, a ratio of intensity of the interference light beam R5 to that of the interference light beam R6 is determined by a phase difference between the object light beam R3 and the reference light beam R4.

The interference light beams R5 and R6 are input to the two-input balanced photodetector 108. The balanced photodetector 108 generates information regarding a change in the ratio of the intensity of the interference light beam R5 to that of the interference light beam R6, and inputs the information to the control unit 110.

The control unit 110 acquires structural data in a depth direction (a Z direction) of the measurement object 200 based on the information about the change in the ratio of the intensity of the interference light beam R5 to that of the interference light beam R6 generated by the balanced photodetector 108. The control unit 110 controls the irradiation optical system 105 to acquire a plurality of structural data pieces in the depth direction while moving the irradiation position of the object light beam R1 along the direction (at least one of an X direction and a Y direction) orthogonal to the depth direction (the Z direction) of the measurement object 200. In other words, the control unit 110 acquires the plurality of structural data pieces at different positions in the depth direction of the measurement object 200 along at least one of the X and Y directions. Then, the control unit 110 connects the plurality of acquired structural data pieces with a position of the structure formed on the surface of the transparent substrate with a structure 106 (e.g., the structures of the grooves 106A and 106B or the step 106C, which will be described later) as a reference to acquire the two-dimensional or three-dimensional tomographic structural data.

According to the optical coherence tomography apparatus 100 of the present disclosure described above, the control unit 110 connects the plurality of structural data pieces at different positions in the depth direction of the measurement object 200 with the position of the structure of the transparent substrate with a structure 106 (e.g., the structures of the grooves 106A and 106B or the step 106C, which will be described later) as a reference to acquire the two-dimensional or three-dimensional tomographic structural data. Thus, even if the initial position at the time of acquiring the structural data in the depth direction is shifted due to the influence of operating conditions such as a light source, the plurality of structural data pieces can be connected more accurately. As a result, it is possible to provide the optical coherence tomography apparatus 100 having positional accuracy which is less susceptible to the operating conditions such as the light sources.

First Example Embodiment

Figure 2:
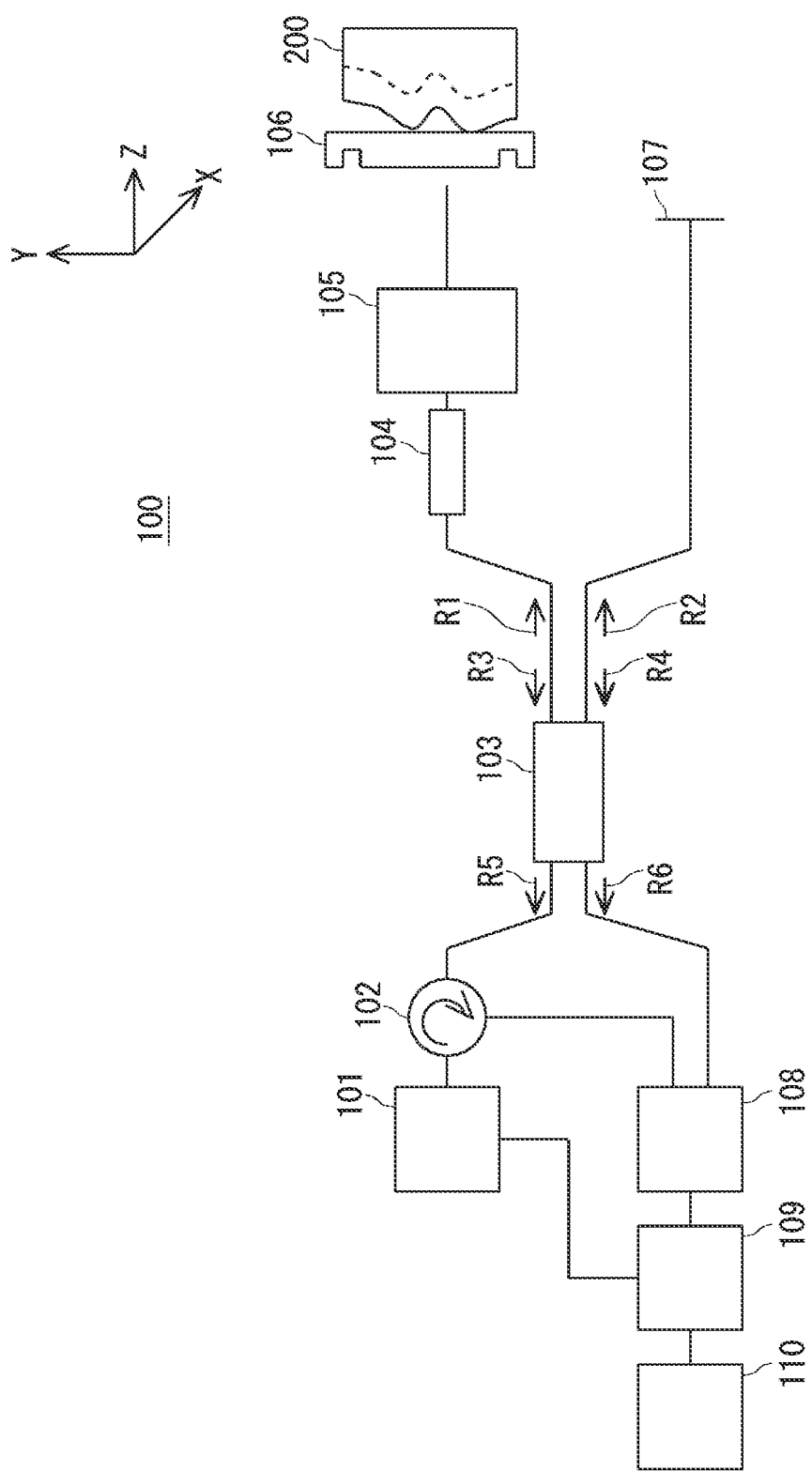
FIG. 2 is a diagram showing an example of an optical coherence tomography apparatus according to a first example example embodiment of the present disclosure.

The optical coherence tomography apparatus 100 according to the first example embodiment of the present disclosure will be described. FIG. 2 is a diagram showing an example of the optical coherence tomography apparatus 100 according to the first example embodiment. As shown in FIG. 2, the optical coherence tomography apparatus 100 includes a wavelength sweeping laser light source 101, a circulator 102, a branching and merging device 103, a fiber collimator 104, an irradiation optical system 105, a transparent substrate with a structure 106, a reference light mirror 107, a balanced photodetector 108, an optical spectrum data generation unit 109, a control unit 110, and so on.

The wavelength sweeping laser light source 101 generates an optical pulse with a swept wavelength. Specifically, the wavelength sweeping laser light source 101 generates optical pulses whose wavelengths increases from 1250 nm to 1350 nm during a duration of 10 μs. The wavelength sweeping laser light source 101 generates the optical pulse repeatedly at 50 kHz every 20 μs.

A light beam emitted from the laser light source 101 passes through the circulator 102 and is branched into an object light beam R1 and a reference light beam R2 in the branching and merging device 103.

The object light beam R1 output from the branching and merging device 103 passes through the fiber collimator 104 and the irradiation optical system 105 composed of a scan mirror and a lens and then enters the transparent substrate with a structure 106. The object light beam R1 incident on the transparent substrate with a structure 106 passes through the transparent substrate with a structure 106 and then is applied to the measurement object 200. Then, the object light beam R1 is scattered by the measurement object 200 and scattered backward (in a direction opposite to an irradiation direction of the object light beam R1) from the measurement object 200. Then, an object light beam (a backscattered light beam) R3 scattered from the measurement object 200 passes through the fiber collimator 104, the irradiation optical system 105, and the transparent substrate with a structure 106, and then returns to the branching and merging device 503.

The reference light beam R2 output from the branching and merging device 103 is reflected by the reference light mirror 107 and then returns to the branching and merging device 103.

Thus, in the branching and merging device 103, the object light beam R3 scattered from the measurement object 200 and the reference light beam R4 reflected from the reference light mirror 107 interfere with each other to obtain the interference light beams R5 and R6. Therefore, a ratio of intensity of the interference light beam R5 to that of the interference light beam R6 is determined by a phase difference between the object light beam R3 and the reference light beam R4.

The interference light beam R5 passes through the circulator 102 and then is input to the two-input photodetector 108, whereas the interference light beam R6 is directly input to the two-input balanced photodetector 108. The balanced photodetector 108 is a photodetector in which two photodiodes are connected in series, and a connection between the photodiodes is an output (a differential output). A band of the balanced photodetector 108 is 1 GHz or less. Further, optical path lengths of the object light beam and the reference light beam from the point where the light beam is branched at the branching and merging device 103 to the point where the object light beam and the reference light beam merge are approximately equal. When there is a large difference in the optical path length of the object light beam and that of the reference light beam, the frequency difference (a wavelength difference) between the object light beams R1 and R3 and the reference light beams R2 and R4 becomes larger than the band of the balanced photodetector 108, which disables the detection of the ratio of the intensity of the interference light beam R5 to that of the interference light beam R6 by the phase difference between the object light beam R3 and the reference light beam R4. When there is a frequency difference between the object light beams R1 and R3 and the reference light beams R2 and R4, the optical path length of the object light and the optical path length of the reference light are adjusted so that the frequency difference becomes smaller than the band of photoelectric conversion of the balanced photodetector 108.

The optical spectrum data generation unit 109 generates an interference light spectrum based on a signal input from the wavelength sweeping laser light source 101 and a signal input from the balanced photodetector 108. Specifically, information about a wavelength change of the light beam emitted from the wavelength sweeping laser light source 101 is input from the wavelength sweeping laser light source 101 to the optical spectrum data generation unit 109. Further, the information about the change in the ratio of the intensity of the interference light beam R5 to that of the interference light beam R6 is input to the optical spectrum data generation unit 109 from the balanced photodetector 108. The optical spectrum data generation unit 109 generates the interference light spectrum based on the information about the wavelength change of the light beam emitted from the wavelength sweeping laser light source 101 and information about the change in the ratio of the intensity of the interference light beam R5 to that of the interference light beam R6. The optical spectrum data generation unit 109 inputs the generated interference optical spectrum to the control unit 110.

The control unit 110 includes a CPU (Central Processing Unit), not shown, and a storage unit, not shown. Then, the CPU executes a program stored in the storage unit, thereby implementing all the processing of the control unit 110.

The programs stored in the respective storage units of the control unit 110 include codes for implementing processing of the control unit 110 by being executed by the CPU. The storage unit includes, for example, any storage device capable of storing this program and various kinds of information used for processing in the control unit 110. The storage device is, for example, a memory or the like.

The program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (Read Only Memory), CD-R, CD-R/W, and semiconductor memories (such as mask ROM, PROM (Programmable ROM), EPROM (Erasable PROM), flash ROM, RAM (Random Access Memory), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g. electric wires, and optical fibers) or a wireless communication line.

Specifically, the control unit 110 controls each unit of the optical coherence tomography apparatus 100.

For example, the control unit 110 controls the irradiation optical system 105 so that the object light beam R1 passes through regions of the transparent substrate with a structure 106 having different thicknesses. The control unit 110 controls a period for which and a speed at which the irradiation optical system 105 scans the measurement object 200.

The control unit 110 performs Fourier transformation on the interference light spectrum generated by the optical spectrum data generation unit 109, thereby acquiring data indicating the intensity of the backscattered light beams (the object light beams) at different positions of the measurement object 200 in the depth direction (the Z direction). Specifically, the control unit 110 calculates wavelength dependence of the intensity of the interference light beams R5 and R6 from the interference light spectrum, and extracts dependence of the intensity of the object light beam R3 scattered from the measurement object 200 on the depth of the measurement object 200 based on the wavelength dependence of the intensity of the interference light beams R5 and R6.

The control unit 110 controls the irradiation optical system 105 to repeatedly perform the A-scan operation while moving the irradiation position of the object light beam R1 in the scanning line direction (the X direction). Then, the control unit 110 connects the measurement results obtained by repeating the A-scan operation while moving the irradiation position of the object light beam R1 in the scanning line direction (the X direction).

The control unit 110 controls the irradiation optical system 105 to repeatedly perform the B-scan operation while moving the irradiation position of the object light beam R1 not only in the scanning line direction but also in the direction perpendicular to the scanning line (the Y direction). Then, the control unit 110 connects the measurement results obtained by repeatedly performing the B-scan operation while moving the irradiation position of the object light beam R1 in the scanning line direction and the direction perpendicular to the scanning line (the Y direction).

As described above, the ratio of the intensity of the interference light beam R5 to that of the interference light beam R6 changes according to the wavelength change of the light beam emitted from the wavelength sweeping laser light source 101. Then, the optical spectrum data generation unit 109 measures the photoelectric conversion output of the balanced photodetector 108 as the interference light spectrum. Further, the control unit 110 performs the Fourier transformation on the interference light spectrum to obtain data indicating the intensity of the backscattered light beams (the object light beams) at different positions in the depth direction (the Z direction) (hereinafter, an operation of obtaining the data indicating the intensity of the backscattered light beams (the object light beams) in the depth direction (the Z direction) at a certain position of the measurement object 200 will be referred to as a "Ascan").

The irradiation position of the object light beam R1 is moved by the irradiation optical system 105, and the measurement object 200 is scanned. The irradiation optical system 105 repeatedly performs the A-scan operation while moving the irradiation position of the object light beam R1 in a scanning line direction (the X direction) and connecting the measurement results, thereby obtaining a map of the intensity of two-dimensional backscattered light beams (the object light beams) in the scanning line direction and the depth direction as the tomographic structural data (hereinafter, an operation of repeatedly performing the A-scan operation in the scanning line direction (the X direction) and connecting the measurement results is referred to as a "B Scan").

Further, the irradiation optical system 105 repeatedly performs the B-scan operation while moving the irradiation position of the object light beam R1 not only in the scanning line direction but also in the direction perpendicular to the scanning line (the Y direction), and connects the measurement results, thereby obtaining three-dimensional tomographic structural data (hereinafter, the operation of repeatedly performing the B-scan operation in the direction perpendicular to the scanning line (the Y direction) and connecting the measurement results is referred to as a "C Scan").

For example, the irradiation optical system 105 scans the measurement object 200 using raster scanning.

More specifically, the interference light spectrum of N samples having a center wavelength $\lambda_0$ and a wavelength range $\Delta\lambda$ is acquired in the A-scan, and the control unit 110 performs the discrete Fourier transformation on the interference light spectrum, thereby obtaining the structural data in the depth direction using $\lambda_0^2/\Delta\lambda$ as a unit of length. When the period of the A-scan is $\Delta T$ and the speed of the object light beam R1 in the B-scan in the scanning line direction is V, structural data (tomographic structural data) in the scanning line direction having $V/\Delta T$ as a unit of length is obtained. In the first example embodiment, for example, measurement is performed with a spatial resolution of about 10 μm in the depth direction and a spatial resolution of about 10 μm in the scanning line direction.

Figure 3A:
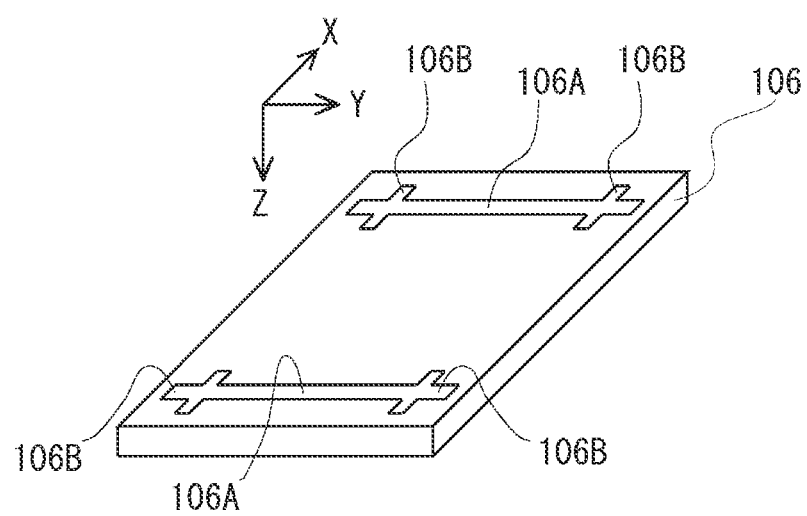
FIG. 3A is a perspective view showing an example of a transparent substrate with a structure according to the first example embodiment of the present disclosure.

FIG. 3A is a perspective view showing an example of the transparent substrate with a structure 106. As shown in FIG. 3A, the transparent substrate with a structure 106 has a structure such as a groove formed on its surface. In the transparent substrate with a structure 106 shown in FIG. 3A, grooves 106A are formed along the short sides (the Y direction) of the transparent substrate with a structure 106 on the surface of the transparent substrate with a structure 106 facing the irradiation optical system 105. Further, grooves 106B extending along the long sides (the X direction) are formed from parts of the grooves 106A on the end side of the grooves 106A of the transparent substrate with a structure 106. The grooves 106A and 106B may be formed on the surface of the transparent substrate with a structure 106 facing measurement object 200. The long sides of the transparent substrate with a structure 106 may extend in the Y direction, and the short sides of the transparent substrate with a structure 106 may extend in the X direction. The width of the grooves 106A and 106B is, for example, 100 μm, and the depth of the grooves 106A and 106B is, for example, 100 μm. In the first example embodiment, since the spatial resolution in the scanning line direction and the depth direction is about 10 μm, the structures of the grooves 106A and 106B having the width and depth described above can be clearly identified in the tomographic structural data. That is, the width and depth of the grooves 106A and 106B in the transparent substrate with a structure 106 are determined in accordance with the desired spatial resolution in the scanning direction and depth direction.

Figure 4A:
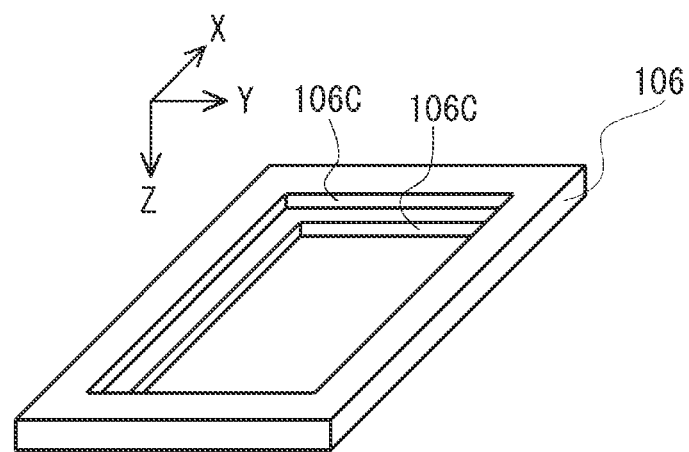
FIG. 4A is a perspective view showing an example of a transparent substrate with a structure according to the first example embodiment of the present disclosure.

FIG. 4A is a perspective view showing another example of the transparent substrate with a structure 106. As shown in FIG. 4A, the transparent substrate with a structure 106 has a structure such as a step formed on its surface. The transparent substrate with a structure 106 shown in FIG. 4A is a transparent frame, and a step 106C is formed along the short sides (the Y direction) and the long sides (the X direction) of the frame on the surface of the frame facing the irradiation optical system 105. Furthermore, the step 106C is formed in such a way that the thickness of the transparent substrate with a structure 106 changes along the direction crossing the short sides (the Y direction) and the long sides (the X direction). More specifically, the step 106C is formed in such a way that the thickness of the transparent substrate with a structure 106 decreases toward the center of the transparent substrate with a structure 106. The step 106C may be formed on the surface of the transparent substrate with a structure 106 facing the measurement object 200. The long sides of the transparent substrate with a structure 106 may extend in the Y direction, and the short sides thereof may extend in the X direction. The width of the step 106C is, for example, 100 μm, and the height of the step 106C is, for example, 100 μm. In the first example embodiment, since the spatial resolution in the scanning line direction and the depth direction is about 10 μm, the structure of the step 106C having the above-described width and height can be clearly identified in the tomographic structural data. That is, the width and height of the step 106C in the transparent substrate with a structure 106 are determined in accordance with the desired spatial resolution in the scanning direction and the depth direction.

Figure 3B:
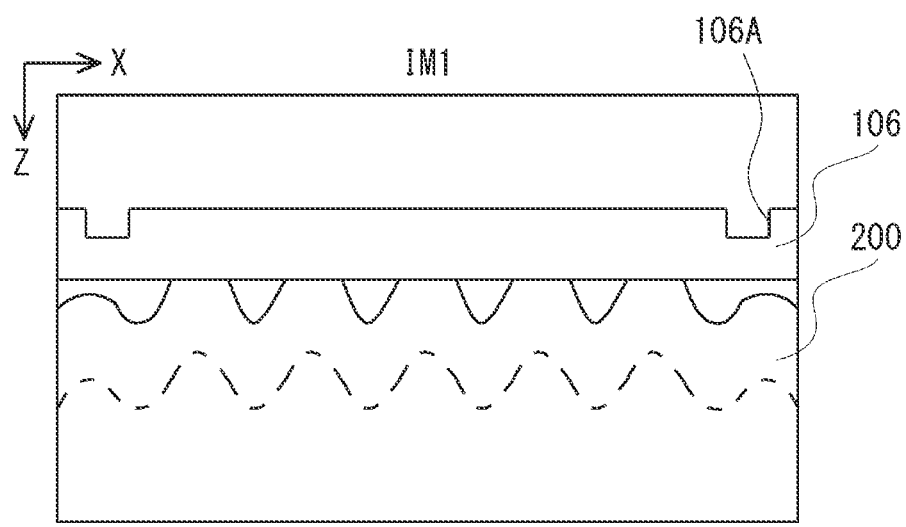
FIG. 3B shows an example of a B-scan image measured in the first example embodiment of the present disclosure.
Figure 4B:
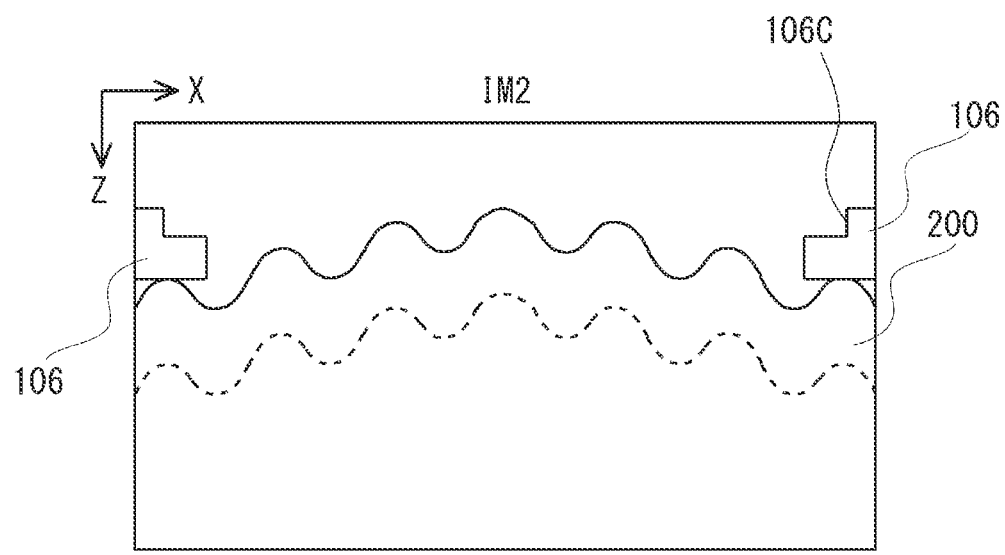
FIG. 4B shows an example of a B-scan image measured in the first example embodiment of the present disclosure.

FIG. 3B shows a B-scan image IM1 obtained by mapping the intensity of the object light beam R3 (the backscattered light beam) scattered from the measurement object 200 in which the transparent substrate with a structure 106 is disposed in front of the measurement object 200, in two dimensions in the X and Z directions. FIG. 4B shows a B-scan image IM2 obtained by mapping the intensity of the object light beam R3 (the backscattered light) scattered from the measurement object 200 in which the transparent substrate with a structure 106 is disposed in front of the measurement object 200, in two dimensions in the X and Z directions. As shown in FIGS. 3B and 4B, with the B-scan image, together with a tomographic image of the measurement object 200, a front surface (a surface of the transparent substrate with a structure 106 facing the irradiation optical system 105) and a back surface (a surface of the transparent substrate with a structure 106 facing the measurement object 200) of the transparent substrate with a structure 106 are observed. Thus, the control unit 110 can connect the structural data obtained by the A-scan with the positions of the front and back surfaces of the transparent substrate with a structure 106 as a reference. Likewise, the control unit 110 can connect the tomographic structural data obtained by the B-scan with the positions of the front and back surfaces of the transparent substrate with a structure 106 as a reference.

Further, since the dimensions of the grooves 106A and 106B or the step 106C formed on the transparent substrate with a structure 106 are known, the control unit 110 can use the dimensions of the grooves 106A and 106B or the step 106C as a reference for the position and length in the X and Z directions. By doing so, the positional accuracy and the length accuracy of the tomographic image of the measurement object 200 are improved. By connecting the B-scan images with high accuracy, the three-dimensional tomographic structural data with high positional accuracy and length accuracy can be obtained.

According to the optical coherence tomography apparatus 100 of the first example embodiment of the present disclosure described above, the control unit 110 connects the plurality of structural data pieces at different positions in the depth direction of the measurement object 200 with the position of the structure of the transparent substrate with a structure 106 (e.g., the structures of the grooves 106A, 106B, or the step 106C, which will be described later) as a reference to acquire the two-dimensional or three-dimensional tomographic structural data. Thus, even if the initial position at the time of acquiring the structural data in the depth direction is shifted due to the influence of operating conditions such as a light source, the plurality of structural data pieces can be connected more accurately. As a result, it is possible to provide the optical coherence tomography apparatus 100 having positional accuracy which is less susceptible to the operating conditions such as the wavelength sweeping laser light source 101, etc.

The control unit 110 controls the irradiation optical system 105 to acquire the plurality of structural data pieces in the depth direction while moving the irradiation position of the object light beam R1 along the two directions (the X and Y directions) orthogonal to the depth direction (the Z direction) of the measurement object 200 and orthogonal to each other. Therefore, the three-dimensional tomographic structural data can be acquired.

The grooves 106A and 106B are formed on the surface of the transparent substrate with a structure 106 along the directions (the X and Y directions) orthogonal to the depth direction (the Z direction). Thus, the depth of the grooves 106A and 106B can be used as a reference of the length in the Z direction. The width of the grooves 106A and 106B can be used as a reference for the length in the X and Y directions. Therefore, the three-dimensional tomographic structural data with both high positional accuracy and high length accuracy can be acquired.

Further, the step 106C may be formed on the surface of the transparent substrate with a structure 106 in such a way that the thickness of the transparent substrate with a structure 106 changes along the directions (the X and Y directions) orthogonal to the depth direction (the Z direction) and along a direction crossing the direction orthogonal to the depth direction. By doing so, the height of the step 106C can be used as a reference of the length in the Z direction. The width of the step 106C can be used as a reference of the length in the X and Y directions. Therefore, the three-dimensional tomographic structural data with both high positional accuracy and high length accuracy can be acquired.

Second Example Embodiment

Figure 5:
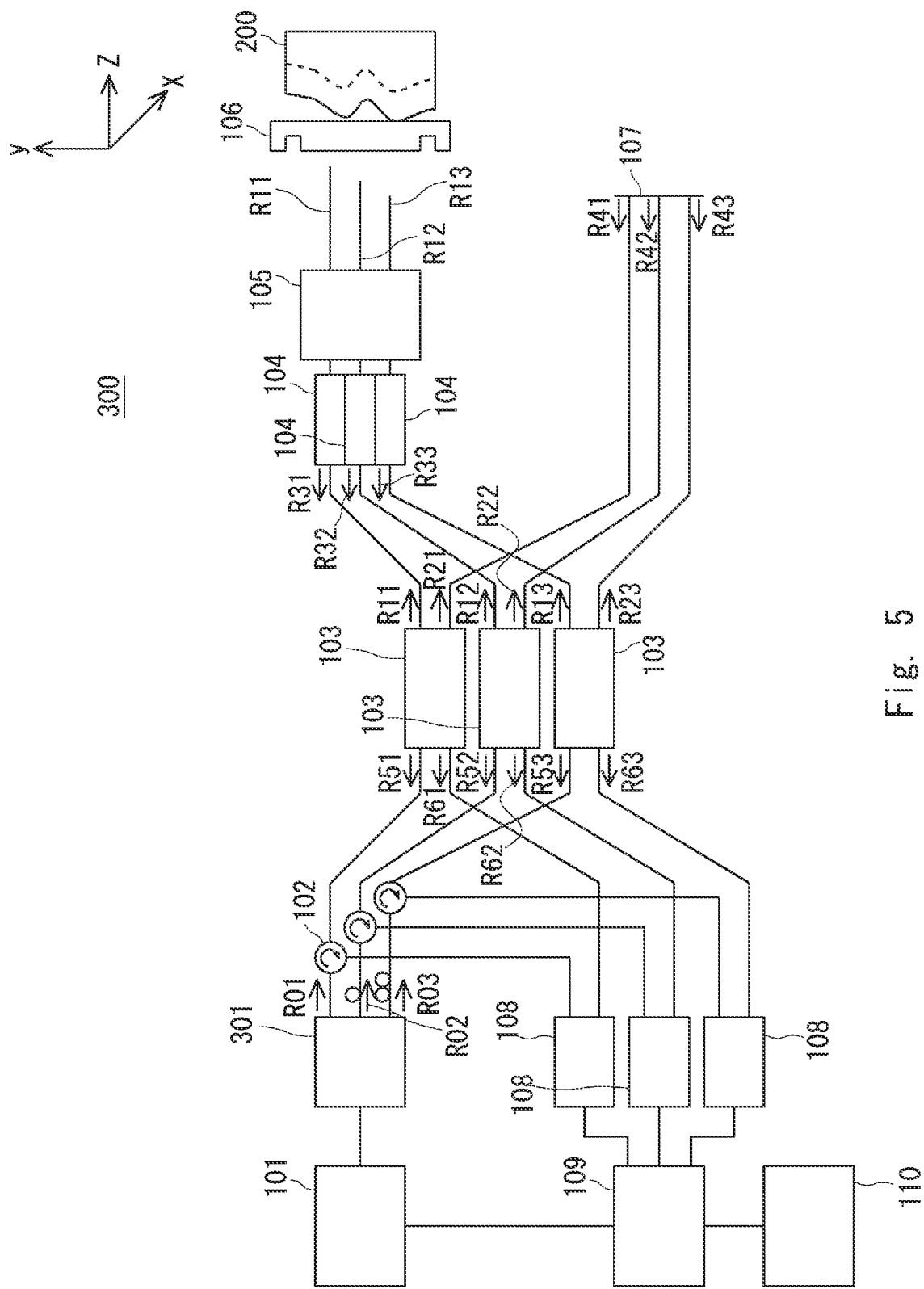
FIG. 5 is a diagram showing an example of an optical coherence tomography apparatus according to a second example embodiment of the present disclosure.
Figure 6:
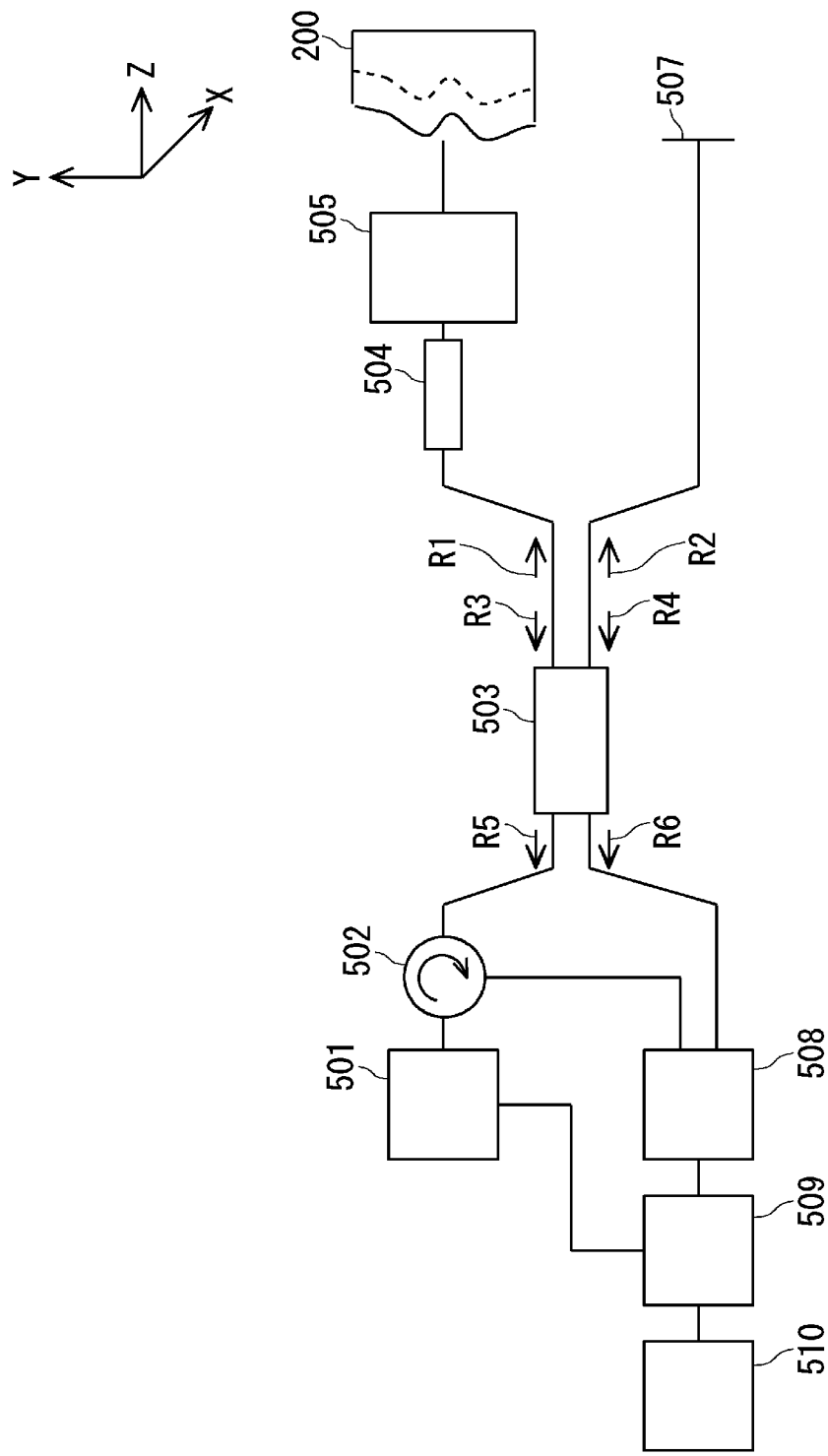
FIG. 6 shows an example of an optical coherence tomography apparatus according to related art.

An optical coherence tomography apparatus 300 according to the second example embodiment of the present disclosure will be described. FIG. 5 is a diagram showing an example of the optical coherence tomography apparatus 300 according to the second example embodiment. As shown in FIG. 5, the optical coherence tomography apparatus 300 includes a wavelength sweeping laser light source 101, a multi-branching device 301 as a second branching unit, a plurality of circulators 102, a plurality of branching and merging devices 103, a plurality of fiber collimators 104, an irradiation optical system 105, a transparent substrate with a structure 106, a reference light mirror 107, a plurality of balanced photodetectors 108, an optical spectrum data generation unit 109, a control unit 110, and so on. Note that the number of circulators 102, the number of branching and merging devices 103, the number of fiber collimators 104, and the number of balanced photodetectors 108 provided in the optical coherence tomography apparatus 300 may be determined in accordance with the number of branches of a light beam emitted from the wavelength sweeping laser light source 101 branched by the multi-branching device 301, and are not limited to those shown in the drawings. Further, the wavelength sweeping laser light source 101, the circulators 102, the branching and merging devices 103, the fiber collimators 104, the irradiation optical system 105, the transparent substrate with a structure 106, the reference light mirror 107, the balanced photodetectors 108, the optical spectrum data generation unit 109, and the control unit 110 included in the optical coherence tomography apparatus 300 according to the second example embodiment are similar to the wavelength sweeping laser light source 101, the circulator 102, the branching and merging device 103, the fiber collimator 104, the irradiation optical system 105, the transparent substrate with a structure 106, the reference light mirror 107, the balanced photodetector 108, the optical spectrum data generation unit 109, and the control unit 110 included in the optical coherence tomography apparatus 100 according to the first example embodiment, respectively, and thus these components according to the second example embodiment are denoted by the same signs as those of the components according to the first example embodiment, and the descriptions of these components according to the second example embodiment will be omitted.

The multi-branching device 301 branches the light beam emitted from the wavelength sweeping laser light source 101 into a plurality of light beams. The multi-branching device 301 imparts different delays (phase differences) to the plurality of branched light beams. In the example shown in FIG. 5, the multi-branching device 301 branches the light beam emitted from the wavelength sweeping laser light source 101 into three light beams R01, R02, and R03, and imparts different delays (phase differences) to the branched light beams.

The plurality of light beams R01, R02, and R03 output from the multi-branching device 301 are input to the corresponding branching and merging devices 102 via the corresponding circulators 103. The plurality of branching and merging devices 103 branch the plurality of input light beams R01, R02, and R03 into object light beams R11, R12, and R13 and reference light beams R21, R22, and R23, respectively.

The plurality of object light beams R11, R12, and R13 output from the branching and merging device 103 pass through the fiber collimators 104 and the irradiation optical system 105 and enters the transparent substrate with a structure 106. The object light beams R11, R12, and R13 incident on the transparent substrate with a structure 106 pass through the transparent substrate with a structure 106, and then are applied to the measurement object 200. More specifically, the irradiation optical system 105 applies the plurality of object light beams R11, R12, and R13 at different positions of the measurement object 200 in the X-Y plane. Then, the object light beams R11, R12, and R13 are scattered by the measurement object 200 and scattered backward (in a direction opposite to an irradiation direction of the object light beams R11, R12, and R13) from the measurement object 200. Object light beams (backscattered light beams) R31, R32, and R33 scattered from the measurement object 200 pass through the fiber collimator 104, the irradiation optical system 105, and the transparent substrate with a structure 106, and then return to the branching and merging device 103.

The plurality of reference light beams R21, R22, and R23 output from the branching and merging device 103 are reflected by the reference light mirror 107 and then return to the branching and merging device 103.

Thus, in the branching and merging device 103, the object light beam R31 scattered from the measurement object 200 and a reference light beam R41 reflected from the reference light mirror 107 interfere with each other to obtain interference light beams R51 and R61. Likewise, in the branching and merging device 103, the object light beams R32 and R33 scattered from the measurement object 200 and reference light beams R42 and R43 reflected from the reference light mirror 107 interfere with each other to obtain interference light beams R52 and R53 and interference light beams R62 and R63, respectively. Therefore, the ratios of the intensity of the interference light beams R51, R52, and R53 to the intensity of the interference light beams R61, R62, and R63, respectively, are determined by the phase difference between the object light beams R31, R32, R33 and the reference light beams R41, R42, and R43, respectively.

The interference light beams R51, R52, and R53 pass through the circulators 102 and then are input to the corresponding balanced photodetectors 108, whereas the interference light beams R61, R62, and R63 are directly input to the corresponding two-input balanced photodetectors 108. Then, information about a change in the ratio of the intensity of the interference light beam R51 to that of the interference light beam R61, information about a change in the ratio of the intensity of the interference light beam R52 to that of the interference light beam R62, and information about a change in the ratio of the intensity of the interference light beam R53 to that of the interference light beam R63 are input to the optical spectrum data generation unit 109 from the plurality of balanced photodetectors 108, respectively.

The optical spectrum data generation unit 109 generates the interference light spectrum based on the information about the wavelength change of the light beam R01 emitted from the wavelength sweeping laser light source 101 and information about the change in the ratio of the intensity of the interference light beam R51 to that of the interference light beam R61. Similarly, the optical spectrum data generation unit 109 generates the interference light spectra based on the information about the wavelength change of the light beams R02 and R03 emitted from the wavelength sweeping laser light source 101 and information about the change in the ratio of the intensity of the interference light beams R52 and R53 to those of the interference light beams R62 and R63, respectively. The optical spectrum data generation unit 109 inputs the generated interference optical spectra to the control unit 110.

The control unit 110 controls the irradiation optical system 105 to apply the plurality of object light beams R11, R12, and R13 at different positions of the measurement object 200 in the X-Y plane.

The control unit 110 performs the Fourier transformation on the interference light spectrum generated by the optical spectrum data generation unit 109, thereby acquiring data indicating the intensity of the backscattered light beams (the object light beams) at different positions in the depth direction (the Z direction) of the measurement object 200 (the A-scan).

Further, the control unit 110 connects the measurement results obtained by repeating the A-scan operation while moving the irradiation positions of the object light beams R11, R12, and R13 in the scanning line direction (the X direction), thereby generating the two-dimensional tomographic structural data in the X and Z directions (the B-scan).

Furthermore, the control unit 110 connects the measurement results obtained by repeating the B-scan operation while moving the irradiation positions of the object light beams R11, R12, and R13 in the scanning line direction and the direction perpendicular to the scanning line (the Y direction), thereby generating the three-dimensional tomographic structural data in the X, Y, and Z directions (the C-scan).

According to the optical coherence tomography apparatus 300 of the second example embodiment described above, the same effects as those of the optical coherence tomography apparatus 100 according to the first example embodiment can be achieved, as a matter of course, and the light beam emitted from the wavelength sweeping laser light source 101 is branched by the multi-branching device 301 into the plurality of light beams R01, R02, and R03, and the plurality of light beams R01, R02, and R03 are branched by the branching and merging device 103 into the plurality of object light beams R11, R12, and R13 and the plurality of reference light beams R21, R22, and R23, respectively. Therefore, the plurality of object light beams R11, R12, and R13 are applied to different positions of the measurement object 200 in the X-Y plane. This makes it possible to obtain a wider range of tomographic structural data of the measurement object 200.

Note that the present disclosure is not limited to the above-described example embodiments, and may be modified as appropriate without departing from the spirit of the disclosure.

Although the present disclosure has been described above with reference to the example embodiments, the present disclosure is not limited by the above. Various modifications that can be understood by a person skilled in the art within the scope of the disclosure can be made to the configurations and details of the present disclosure.

This application claims priority on the basis of Japanese Patent Application No. 2018-212046, filed Nov. 12, 2018, the entire disclosure of which is incorporated herein by reference.

INDUSTRIAL APPLICABILITY

It is possible to provide an optical coherence tomography apparatus, an imaging method, and an imaging program, which have positional accuracy which is less susceptible to operating conditions such as a light source.

REFERENCE SIGNS LIST 100, 300 OPTICAL COHERENCE TOMOGRAPHY APPARATUS
101 WAVELENGTH SWEEPING LASER LIGHT SOURCE
102 CIRCULATOR
103 BRANCHING AND MERGING DEVICE (FIRST BRANCHING UNIT)
104 FIBER COLLIMATOR
105 IRRADIATION OPTICAL SYSTEM (IRRADIATION UNIT)
106 TRANSPARENT SUBSTRATE WITH STRUCTURE
106A, 106B GROOVE
106C STEP
107 REFERENCE LIGHT MIRROR
108 BALANCED PHOTODETECTOR (MEASUREMENT UNIT)
109 OPTICAL SPECTRUM DATA GENERATION UNIT
110 CONTROL UNIT
301 MULTI-BRANCHING DEVICE (SECOND BRANCHING UNIT)
R1, R3, R11, R12, R13, R31, R32, R33 OBJECT LIGHT BEAM
R2, R4, R21, R22, R23, R41, R42, R43 REFERENCE LIGHT BEAM
R5, R6, R51, R52, R53, R61, R62, R63 INTERFERENCE LIGHT BEAM
200 MEASUREMENT OBJECT

What is claimed is:

1. An optical coherence tomography apparatus comprising:
a wavelength sweeping laser light source;
a branching and merging device configured to branch a light beam emitted from the wavelength sweeping laser light source into an object light beam and a reference light beam;
an irradiation optical system configured to apply the object light beam to a predetermined scanning range of a measurement object;
a transparent substrate disposed between the measurement object and the irradiation optical system,
wherein the transparent substrate is configured to transmit the object light beam;
a balanced photodetector configured to generate information about a change in an intensity ratio of interference light beams, the interference light beams being generated by the interference between the object light beam and the reference light beam,
wherein the object light beam is scattered from the measurement object after being transmitted through the transparent substrate and then being applied to the measurement object; and
a computer configured to acquire structural data of the measurement object in a depth direction using the information about the change in the intensity ratio of the interference light beams generated by the balanced photodetector,
wherein the transparent substrate comprises a structure configured to change a thickness of the transparent substrate,
wherein the structure is on a surface of the transparent substrate,
wherein the transparent substrate comprises a frame disposed parallel to a direction orthogonal to the depth direction,
wherein the structure comprises a plurality of steps formed in such a way that the thickness of the transparent substrate gradually changes toward a center of the transparent substrate,
wherein the computer is configured to control the irradiation optical system to acquire a plurality of pieces of the structural data in the depth direction while moving an irradiation position of the object light beam along a direction orthogonal to the depth direction of the measurement object, and
wherein the computer is configured to connect the acquired plurality of pieces of the structural data in the depth direction with a position of the structure as a reference.

2. The optical coherence tomography apparatus according to claim 1, wherein the computer is configured to control the irradiation optical system to acquire the plurality of pieces of the structural data in the depth direction while moving the irradiation position of the object light beam along two directions orthogonal to the depth direction of the measurement object and orthogonal to each other.

3. The optical coherence tomography apparatus according to claim 2, wherein the plurality of steps are formed along to the two directions.

4. The optical coherence tomography apparatus according to claim 1, further comprising a multi-branching device disposed between the wavelength sweeping laser light source and the branching and merging device and configured to branch the light beam emitted from the wavelength sweeping laser light source into a plurality of light beams,
wherein the branching and merging device is configured to branch each of the plurality of light beams output from the multi-branching device into an object light beam and a reference light beam, and
wherein the irradiation optical system is configured to apply the plurality of object light beams output from the branching and merging device to different positions on the surface of the measurement object.

5. An imaging method comprising:
branching a light beam emitted from a wavelength sweeping laser light source into an object light beam and a reference light beam;
applying the object light beam to a predetermined scanning range of a measurement object through a transparent substrate including a structure configured to change a thickness of the transparent substrate,
wherein the structure is on a surface of the transparent substrate,
wherein the transparent substrate comprises a frame disposed parallel to a direction orthogonal to the depth direction, and
wherein the structure comprises a plurality of steps formed in such a way that the thickness of the transparent substrate gradually changes toward a center of the transparent substrate;
generating information about a change in an intensity ratio of interference light beams, the interference light beams being generated by the interference between the object light beam scattered from the measurement object and the reference light beam;
acquiring, by a computer, structural data of the measurement object in a depth direction using the information about the change in the intensity ratio of the interference light beams;
acquiring, by the computer, a plurality of pieces of the structural data in the depth direction while moving an irradiation position of the object light beam along a direction orthogonal to the depth direction of the measurement object; and
connecting, by the computer, the acquired plurality of pieces of the structural data in the depth direction with a position of the structure as a reference.

6. The method according to claim 5, wherein the computer is configured to acquire the plurality of pieces of the structural data in the depth direction while moving the irradiation position of the object light beam along two directions orthogonal to the depth direction of the measurement object and orthogonal to each other.

7. The method according to claim 6, wherein the plurality of steps are formed along to the two directions.

8. The imaging method according to claim 5, further comprising:
branching the light beam emitted from the wavelength sweeping laser light source into a plurality of light beams;
branching each of the plurality of light beams into an object light beam and a reference light beam; and
applying the plurality of object light beams to different positions to a surface of the measurement object.

9. A non-transitory computer readable medium storing an imaging program, which if executed, causes a computer to execute operations comprising:
acquiring structural data of a measurement object in a depth direction using information about a change in an intensity ratio of interference light beams,
wherein the interference light beams are generated by interference between an object light beam and a reference light beam,
wherein the object light beam is scattered from the measurement object, after the object light beam branched from a light beam emitted from a wavelength sweeping laser light source and then passes through a transparent substrate including a structure configured to change a thickness of the transparent substrate, the structure being on a surface of the transparent substrate, and then is applied to a predetermined scanning range of the measurement object, and
wherein the reference light beam is branched from the light beam emitted from the wavelength sweeping laser light source;
acquiring a plurality of pieces of the structural data in the depth direction while moving an irradiation position of the object light beam along a direction orthogonal to the depth direction of the measurement object; and
connecting the acquired plurality of pieces of the structural data in the depth direction with a position of the structure as a reference,
wherein the transparent substrate comprises a frame disposed parallel to a direction orthogonal to the depth direction, and
wherein the structure comprises a plurality of steps formed in such a way that the thickness of the transparent substrate gradually changes toward a center of the transparent substrate.

10. A non-transitory computer readable medium storing the imaging program according to claim 9, the operations further comprising:
acquiring the plurality of pieces of the structural data in the depth direction while moving the irradiation position of the object light beam along two directions orthogonal to the depth direction of the measurement object and orthogonal to each other.

11. A non-transitory computer readable medium storing the imaging program according to claim 10, wherein the plurality of steps are formed along to the two directions.

12. A non-transitory computer readable medium storing the imaging program according to claim 9, the operations further comprising:
applying a plurality of branched object light beams from among a plurality of the light beams branched from the light beam emitted from the wavelength sweeping laser light source to different positions on a surface of the measurement object.

* * * * *